United States Patent [19]
Senn et al.

[11] Patent Number: 5,571,947
[45] Date of Patent: Nov. 5, 1996

[54] MEASURING ASSEMBLY FOR STUDYING GASEOUS MEDIA

[75] Inventors: Jürgen Senn, Freiburg; Kurt Strnad, Lenzkirch, both of Germany

[73] Assignee: Testo GmbH & Co., Lenzkirch, Germany

[21] Appl. No.: 436,149

[22] Filed: May 8, 1995

[30]  Foreign Application Priority Data

May 20, 1994 [DE] Germany .......................... 44 17 665.1

[51] Int. Cl.⁶ .............................. B01L 3/00; G01N 27/56
[52] U.S. Cl. ........................ 73/31.05; 73/23.2; 422/104; 422/49; 422/83
[58] Field of Search ................. 73/31.05, 23.2; 422/83, 94, 99, 102, 104, 49

[56]  References Cited

U.S. PATENT DOCUMENTS

| | | | |
|---|---|---|---|
| 4,597,850 | 7/1986 | Takahasi et al. | 204/426 |
| 4,916,934 | 4/1990 | Nagata et al. | 73/23 |
| 5,363,690 | 11/1994 | Evangelista et al. | 73/31.05 |
| 5,368,820 | 11/1994 | Lautenschlager | 422/102 |
| 5,397,442 | 3/1995 | Wachsman | 204/153.16 |
| 5,419,874 | 5/1995 | Coassin et al. | 422/134 |

FOREIGN PATENT DOCUMENTS

| | | |
|---|---|---|
| 2618738 | 4/1976 | Germany . |
| 3007904 | 3/1980 | Germany . |

*Primary Examiner*—Hezron E. Williams
*Assistant Examiner*—J. David Wiggins
*Attorney, Agent, or Firm*—Cowan, Liebowitz & Latman, P.C.

[57]  ABSTRACT

A measuring assembly is described for studying gaseous media, in which a measuring cell (20) connected to a circuit board (40) is clamped into a receptacle (10). The receptacle (10) includes a base plate (11), a pressure plate (30), arms connecting base plate (11) and the pressure plate (30) with each other, i.e., a stud bolt (13) and a connecting arm (14), as well as a pressure spring (16) acting on the pressure plate (30). The pressure plate (11) is supplemented by a chamber cover (15) so as to form a gas chamber (17). Preferably, a filter (50) is located between the base plate (11)/chamber cover (15) and the measuring cell (20).

8 Claims, 4 Drawing Sheets

MEASURING ASSEMBLY FOR STUDYING GASEOUS MEDIA

FIELD OF INVENTION

The invention relates to a measuring assembly for studying gaseous media.

BACKGROUND OF THE INVENTION

Measuring assemblies of this type are provided with measuring cells or measuring sensors, e.g. electrochemical gas sensors, that are used to study gaseous media, in particular toxic and non-toxic gases. Usually, the measuring cells are attached by means of releasable screw connections to the gas-conducting channels or measuring chambers. These types of attachments, which use screws distributed over the circumference of the measuring cell, result in the following problems that are particularly critical, due to the fact that the measuring cells must be replaced after a certain operating time or in case of a defect.

If the screws are not uniformly tightened when attaching the measuring cell, an uneven surface pressure may result, possibly causing leakages in the measuring system. Since air entering through a leak reaches the measuring cells via these leakages, the measuring result is distorted.

The uneven pressure furthermore leads to distortions of the measuring cell or sensor housing, possibly resulting in tears in the material. These tears permit air entering through leakages to reach the measuring system, or alternatively, liquid may drain from the interior of the measuring cell. Both defects lead to distortions of the measuring value and, ultimately, to the unfitness of the measuring cell.

These disadvantages can be avoided only if the attachment screws are tightened to comply with a maximum torque value by using a torque wrench, which is not generally available to the user. Furthermore, during a measuring cell replacement, care must be taken that the attachment screws be tightened diagonally, in order to attain a uniform distribution of sealing pressure.

Another disadvantage is that the effects of mechanical force on the measuring cell housing or on the circuit board of the evaluation circuit, if the latter is mechanically connected to the measuring cell housing, lead to distortions in the measuring values. This means, however, that following a measuring cell replacement, the measuring system must again be adjusted. This usually requires a test gas that is frequently not available to the user.

In practice, this problem is solved by the measuring cell being adjusted at the factory and labeled with a corresponding coefficient that can be used to set the evaluation circuit of the respective measuring cell after installation has been completed, without the application of test gas. But such an adjustment presupposes identical and reproducible installation conditions in the measuring cell, equal to those coefficients determined at the factory. If this is not ensured, measuring errors will again occur.

To avoid these errors, two important boundary conditions must be met. On one hand, the assembly must be constructed so that the measuring cell can be mounted in a reproducible manner, always under the same conditions. On the other hand, the evaluation and processing electronics must be connected to the measuring cell in such a way that no later adjustment by the user is required.

It is indeed known that the circuit boards with a signal evaluation circuit are supplied with the measuring cell to which they are electrically connected. But if a secure connection between the measuring cell and circuit board is not made, vibrations during insertion may result in contact problems, and thus in measuring errors. Screwing the circuit board to the measuring cell causes problems, since mechanical bending strains may lead to tearing and/or measuring errors.

The invention at hand is thus based on the task of creating a measuring assembly that enables a problem-free exchange of the adjusted measuring cell with the signal evaluation circuit, and Which is constructed to prevent installation errors leading directly or indirectly to measuring value distortions.

SUMMARY OF THE INVENTION

This task is solved, according to this invention, by securely connecting the measuring cell to the circuit board carrying the evaluation circuit, and by installing this unit in a receptacle that ensures uniform and reproducible pressure loads on both the measuring cell and the circuit board. With this type of measuring cell attachment, the user can be provided with a precisely adjusted measuring cell that can be used after replacement, without any further adjustment or setting.

In an illustrative embodiment of this invention, the receptacle comprises a base plate and a pressure plate, between which the measuring cell with the circuit board is clamped. The pressure plate, which is connected in a releasable manner to the base plate via connecting arms, rests evenly, e.g., with pressure supports or a thrust collar, on the measuring cell under the action of a pressure spring with a defined spring tension. These pressure elements may rest directly on the surface of a measuring cell or, as is further suggested, may engage, as a result of external force, with channels or receptacles provided on the measuring cell.

In a further aspect of this invention, it is useful that the pressure spring include a plate spring suspended at both ends in the connecting arms that extend parallel to the axis. The plate spring is positioned at two points and is designed so that it presses the measuring cell with a predefined force against the base plate by means of the pressure plate. The plate spring is suspended at one side in a stud bolt, and on the other side is connected to a hook-shaped end of an arm that is linked so that it may swivel to the base plate. Such a mounting enables the user to replace the measuring cell with one hand motion and without using tools, by simply unhooking the plate spring.

It would also be conceivable that the spring element itself is permanently connected, e.g., via a hinge, to the stud bolt. The arrangement of the pressure plate and/or stud bolt could also be replaced with a one-piece housing part. Also conceivable would be other designs of the spring element, according to which a type of bayonet closure would be provided instead of the hook-shaped connection.

In a still further feature of this invention, the circuit board carrying the signal processing circuit is directly connected, both electrically and mechanically, to the measuring cell. This eliminates sensitive conductor connections that, in cases of low currents and voltages, frequently lead to distortions of measuring values. The circuit board is also secured mechanically since it is fixed between the measuring cell and the pressure plate. Consequently, suitable memory media may be provided on it, e.g., an EPROM, in which the adjustment data for the specific measuring cell are saved, and whereby the total assembly can be adjusted at the factory. The user, as a result, can install the entire unit into his measuring system and operate it without any adjustment.

According to another aspect of this invention, the pressure plate, together with a chamber cover, forms a gas-tight chamber with inlet and outlet sockets. By means of these inlet and outlet sockets, adjoining and successive measuring cells can be connected to each other by means of couplings, so that the user can assemble a complete, modular measuring system with a few hand motions.

In another feature of this invention, the assembly according to the invention furthermore allows for the insertion of a filter between the measuring cell and the base plate or the mentioned gas chamber, the filter being equipped with the same retention and adjustment means as the measuring cell itself. By means of such filters it is possible, e.g., to suppress cross-sensitivities of the respective measuring cells. Installation and removal of this filter is accomplished in the same simple manner, without tools.

The overall construction of the measuring assembly is such that, due to the spring force acting on the measuring cell, a high degree of impact and vibration indifference is achieved, which is of particular advantage for portable measuring instruments. This construction also guarantees that the measuring cell function independently from its position.

DESCRIPTION OF THE DRAWINGS

The invention is described in detail below using a preferred embodiment that is shown in the drawings, in which.

DESCRIPTION OF THE PREFERRED EMBODIMENT OF THE INVENTION

Figure 1:
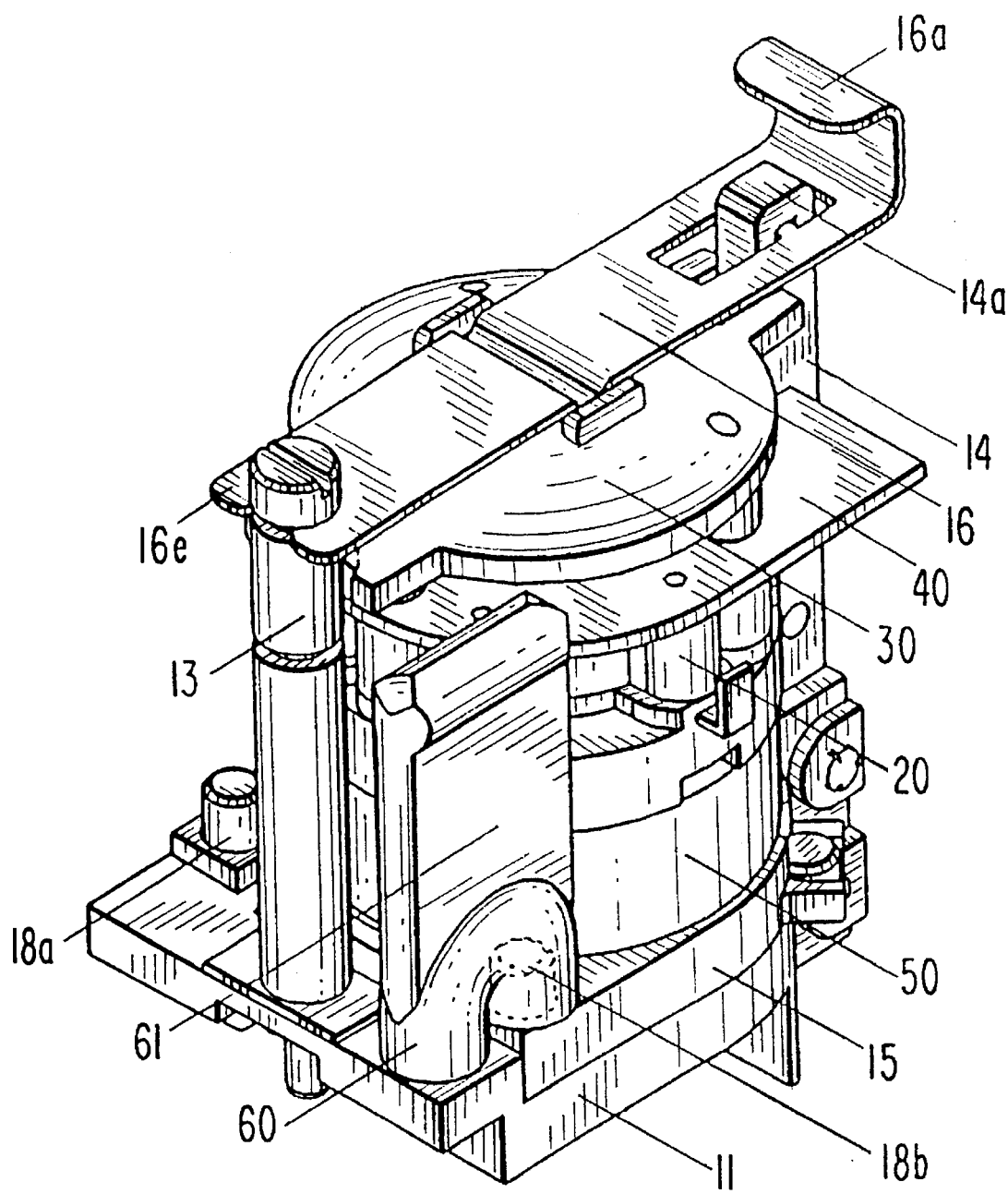
FIG. 1 shows a perspective view of the measuring assembly.

Referring now to the drawings and in particular to FIG. 1, the measuring assembly comprises a receptacle 10 with a base plate 11, a stud bolt 13, a connecting arm 14, a pressure spring 16, and a pressure plate 30. A measuring cell 20 with a circuit board 40 and a filter 50 that are mounted on it are clamped between these elements. The base plate 11 is connected with a chamber cover 15, which together with the former define a gas chamber 17, as shown in FIG. 4.

Figure 3:
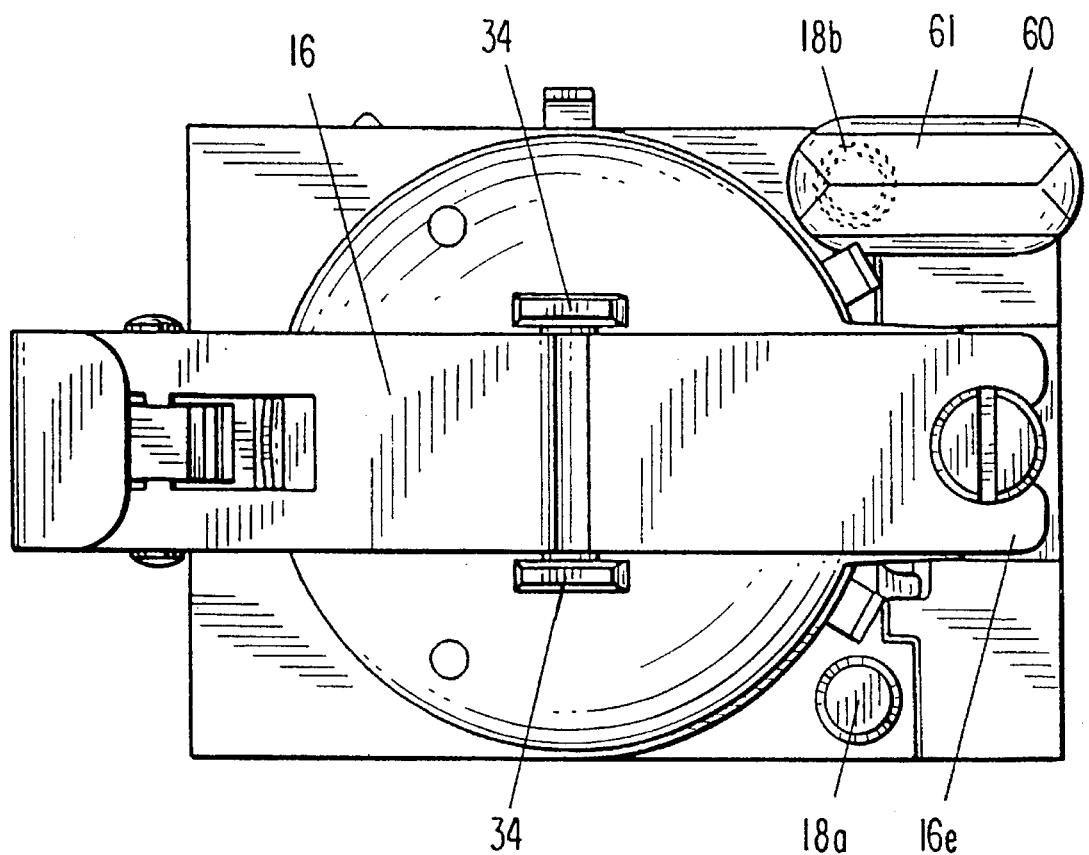
FIG. 3 shows a top view of the assembly of FIGS. 1 and 2.
Figure 4:
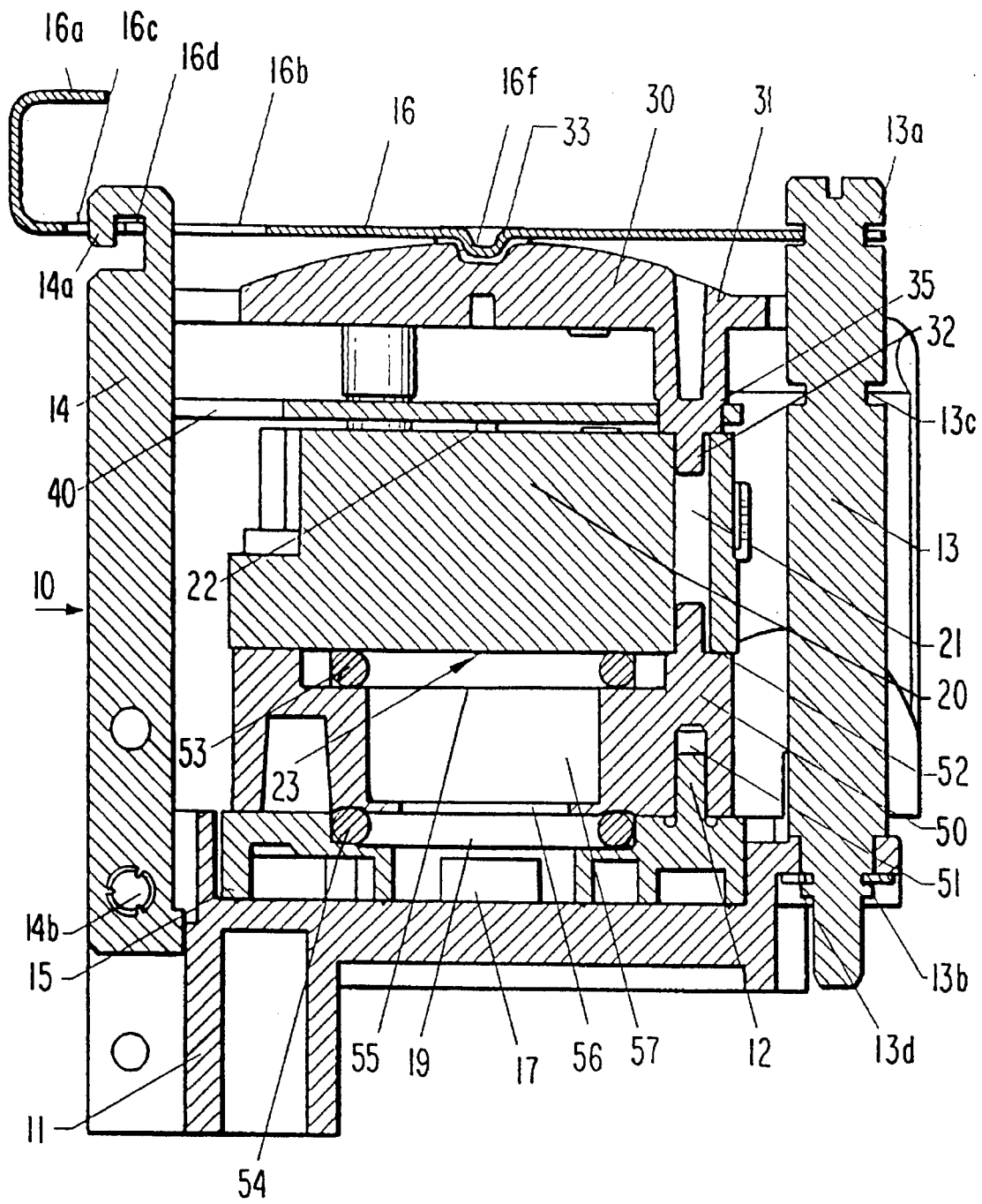
FIG. 4 shows an axial section of the assembly.

The stud bolt 13 is inserted with its lower end into a bore in the base plate 11 and is fixed on the latter with a retaining ring 13d inserted into a ring groove 13b, as shown in FIG. 4. At its upper end, it has another ring groove 13a, into which the pressure spring 16 has been inserted in a releasable manner with its fork-shaped end 16e, as shown in FIG. 3.

Opposite the stud bolt 13 is the connecting arm 14, which is connected so that it may swivel via hinge bolt 14b, as shown in FIG. 4, to the base plate 11. The upper, free end of this connecting arm 14 is constructed as a catch hook 14a that engages with break-throughs 16b and 16c of the pressure spring 16 and encompasses a bar 16d in the closed state. The end of pressure spring 16 that adjoins this catch hook 14a is bent into a U-shape in order to form an operating nose 16a that facilitates handling. The catch hook 14a can be released by pressing down on the operating nose 16a. Pressure spring 16 has in its middle section a downward bend 16f that engages in a force-derived and form-fitting manner with a catch receptacle 33 of the pressure plate 30. Guide bars 34 that extend parallel to the pressure spring 16 are provided on the pressure plate 30 in order to secure the lateral position.

The constructive design of the sensor receptacle 10 ensures, as shown in FIG. 4, identical and reproducible clamping, and thus load conditions, even after a measuring cell replacement. The measuring cell 20 itself is connected directly to the circuit board 40 carrying the signal conditioning circuit, i.e., via several contact pins 22 that engage with contact bushings provided in the circuit board 40, and thus serve both as a mechanical and electrical connection. Circuit board 40 is secured axially in its position, without pressure load, by means of ring collars 35 on supports 31.

For a direct transmission of the clamping pressure from the pressure plate 30 to the measuring cell 20, the circuit board 40 is provided with break-throughs, through which pressure supports 31 extend without being affected by external force. Pressure supports 31 rest with their end faces on the top of the measuring cell 20 and engage, for centering and position adjustment, with their noses 32 in the axis-parallel channels 21 of the measuring cell 20.

In the embodiment shown in FIG. 4, the filter 50 has been interposed between the base plate 11 and the measuring cell 20, while a chamber 57 holding the filter material (not shown) is bordered on both sides by a pair of gas-permeable filter membranes 55 and 56. Filter chamber 57 is arranged so that it is able to communicate with a gas inlet opening 23 of the measuring cell 20. Filter 50 is provided on its top with upwards extending guide pins 52 that are constructed and arranged similarly to the noses 32 of the pressure plate 30. This also ensures a reproducible position securement and alignment of the filter 50 in respect to the measuring cell 20.

For further alignment, the filter 50 is provided with pocket hole-like receptacles 51 that are oriented in the same manner as channels 21 of the measuring cell 20, and that engage with guide pins 12 associated with the base plate 11. In the shown embodiment, these guide pins 12 are part of the chamber cover 15, which is set onto the base plate 11 in order to form the gas chamber 17.

Gas chamber 17 is also provided with a central opening 19 that is associated with filter chamber 57. Sealing rings, preferably O-rings 53 and 54, which have been inserted between the measuring cell 20 on one side and the chamber cover 15 on the other side, ensure a gas-tight closure of the system.

Figure 2:
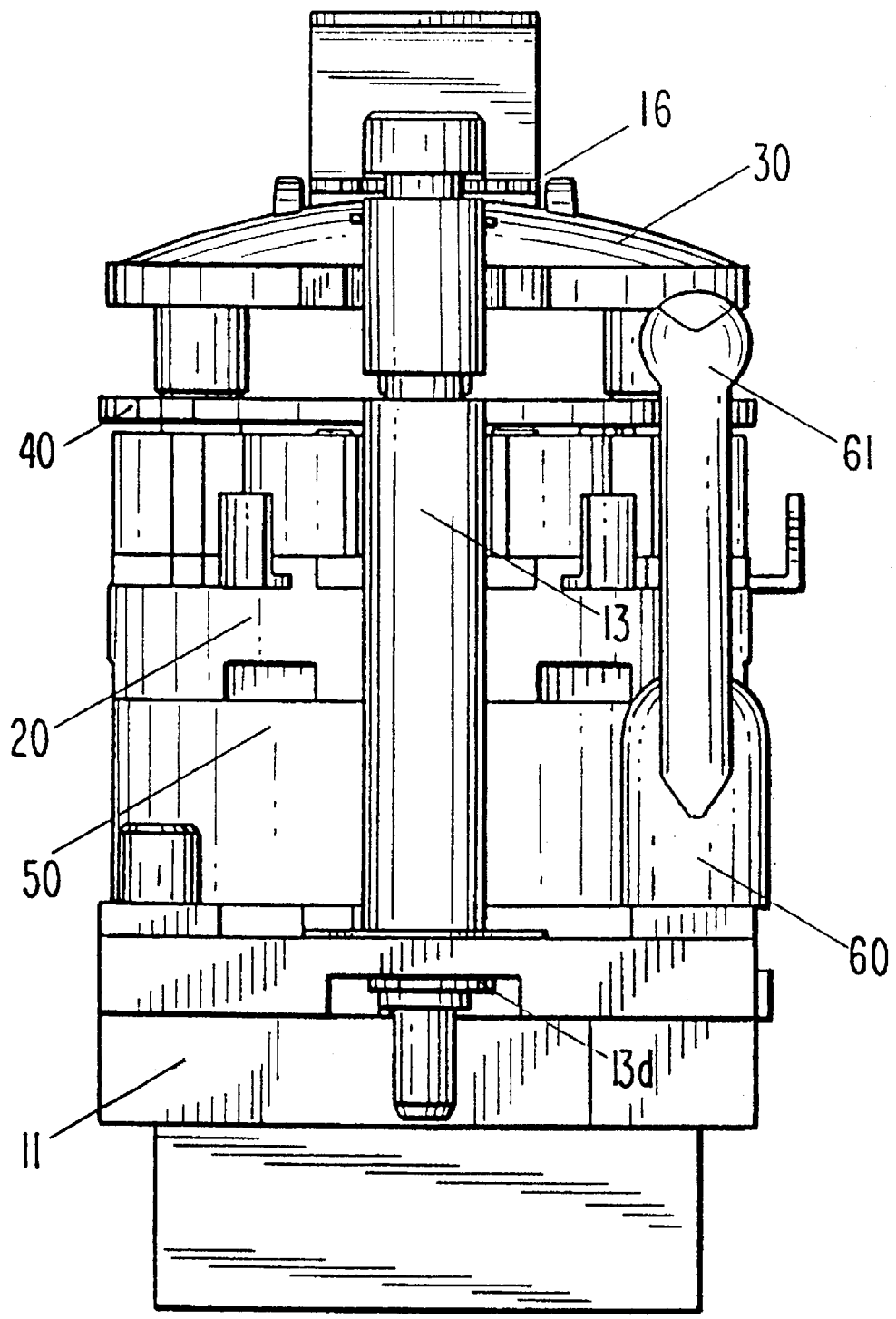
FIG. 2 shows a side view of the assembly of FIG. 1, viewed from the left.

The gas is fed into and discharged from the chamber 17 via inlet and outlet sockets 18a and 18b, as shown in FIG. 3, that are open towards the top and onto which couplings 60 can be placed. These couplings 60, which are equipped with a handle piece 61 at their top as shown in FIGS. 2 and 3, can be turned around the axis of the inlet or outlet sockets 18a or 18b, so that they can be used to connect consecutive receptacles 10 with each other. In this way, a number of measuring assemblies according to the invention can be used to assemble a completely open and expandable measuring system.

The following advantages are attained with the above explained measuring assembly according to the invention.
1. Replacement of the measuring cell 20 and the circuit board 40 without using special tools.

2. Uniform pressure load on the measuring cell 20 and the circuit board 40 that has been attached to the measuring cell 20 without pressure but is securely positioned, so that during a replacement, measuring cell-circuit board units that have already been factory-adjusted can be inserted and operated without any further adjustment.

3. No risk of signal distortions due to mechanical tensions following the installation.

4. As a result of the modular construction provided, it is possible to install measuring cells 20 and filters 50 of different types, as long as the dimensions given by the receptacle are complied with.

5. Several measuring assemblies can be combined into a register with different measuring cells 20.

6. The measuring cells 20 fixed in the sensor receptacle 10 can be mounted and operated independently from their position.

We claim:

1. A measuring assembly for sensing gaseous media, comprising:
   a) an electrical measuring cell having an inlet opening for introducing gas thereto and an outlet for dismissing gas therefrom for generating electrical signals in accordance with the concentration and/or composition of the gaseous medium introduced to said measuring cell;
   b) a signal processing circuit connected to said measuring cell for receiving and evaluating said electrical signals, said circuit being arranged on a circuit board;
   c) a receptacle including a base plate and a cover plate between which said measuring cell is located;
   d) means for electrically and mechanically connecting said circuit board to the said measuring cell in a releasable manner so that said measuring cell with said circuit board is disposed between said base plate and said cover plate whereby said measuring cell may be readily replaced with another;
   e) said cover plate comprising a pressure plate constructed to press said measuring cell against said base plate with a uniform pressure distribution; and
   f) a pressure spring connected in a retaining position to said receptacle to abut an adjacent surface of said pressure plate and to impose a defined tension on a said pressure plate and movable from said retaining position to permit the replacement of said measuring cell.

2. The measuring assembly as claimed in claim 1, wherein there is further included a first connecting arm having a first end connected rigidly to said base plate and a second end connected to a ring groove, a second connecting arm having a first end connected in partially free manner so that it may swivel with respect to said base plate and a second, partially free end connected to a catch hook, said pressure spring being constructed as a plate spring with a bend projecting therefrom to engage and to exert a force on said adjacent surface of said pressure plate, said pressure spring being set in a releasable manner and having a first end constructed as a fork in said ring groove and a second end connected to an opening, said opening engaging said catch hook of said second connecting arm in a releasable manner.

3. The measuring assembly as claimed in claim 2, wherein said pressure plate includes at its top surface a catch receptacle, said catch receptacle engaging with said plate spring by means of its bend and bars disposed on both sides of said plate spring adjoining said catch receptacle.

4. The measuring assembly as claimed in claim 2, wherein said pressure plate includes pressure supports, said pressure supports disposed to rest on said measuring cell, said circuit board disposed with respect to said measuring cell to face said pressure plate, said circuit board including recesses corresponding to said pressure supports, said measuring cell having axially extending channels for engaging said pressure supports in a form-fitting manner, said pressure supports having noses offset thereto.

5. The measuring assembly as claimed in claim 1, wherein there is further included a chamber cover disposed adjacent a surface of said measuring cell remote from said pressure plate to form a gas-tight chamber within said chamber cover, and said chamber having an inlet and an outlet socket, said chamber having a central opening for communicating with said gas inlet opening of said measuring cell.

6. The measuring assembly as claimed in claim 5, wherein there is further included a coupling for connecting a plurality of adjoining, consecutive measuring cells, said coupling interconnecting an outlet socket of one of said plurality of measuring cells to said inlet socket of said adjourning, consecutive measuring cell of said plurality.

7. The measuring assembly as claimed in claim 4, wherein there is included a filter inserted between said measuring cell and said base plate, said filter having receptacles corresponding to said channels of said measuring cell, guide pins corresponding to said guide pins of said chamber cover, a chamber for receiving therein a filter, said chamber having a central opening and being disposed between said central opening and said gas inlet opening of said measuring cell.

8. The measuring assembly as claimed in claim 7, wherein said measuring cell has axially extending channels, and said chamber cover has guide pins extending axially from said surface to engage with said channels of said measuring cell or said receptacles of said filter.

* * * * *